United States Patent [19]

Chang et al.

[11] Patent Number: 5,077,069

[45] Date of Patent: Dec. 31, 1991

[54] COMPOSITION OF NATURAL ANTIOXIDANTS FOR THE STABILIZATION OF POLYUNSATURATED OILS

[75] Inventors: Stephen S. Chang, East Brunswick, N.J.; Kejian Wu, St. Paul, Minn.

[73] Assignee: Kabi Pharmacia AB, Stockholm, Sweden

[21] Appl. No.: 638,063

[22] Filed: Jan. 7, 1991

[51] Int. Cl.$^5$ .......................... A23B 4/14; A23B 5/08; A23B 9/16; A23D 7/06

[52] U.S. Cl. ................. 426/330.6; 426/541; 426/654

[58] Field of Search ............ 426/541, 542, 330.6, 426/648, 654, 262, 268, 270

[56] References Cited

U.S. PATENT DOCUMENTS

| | | | |
|---|---|---|---|
| 2,768,084 | 10/1956 | Griffith | 426/541 |
| 2,772,169 | 11/1956 | Hall | 426/541 |
| 3,305,366 | 2/1967 | Sutton | 426/262 |
| 3,852,502 | 12/1974 | Bishov | 426/542 |
| 3,950,266 | 4/1976 | Chang | 426/542 |
| 4,011,348 | 3/1977 | Farrier | 426/268 |
| 4,012,531 | 3/1977 | Viani | 426/542 |
| 4,110,483 | 8/1978 | Bishov | 426/542 |
| 4,363,823 | 12/1982 | Kimura | 426/542 |
| 4,380,506 | 4/1983 | Kimura | 426/542 |
| 4,476,112 | 10/1984 | Aversano | 426/654 |
| 4,477,478 | 10/1984 | Tiberio | 426/330.6 |
| 4,839,187 | 6/1989 | Mai | 426/542 |
| 4,877,635 | 10/1989 | Todd | 426/542 |
| 4,891,231 | 1/1990 | Mai | 426/542 |
| 4,925,681 | 5/1990 | Mai | 426/542 |
| 4,988,522 | 1/1991 | Warren | 426/268 |
| 4,988,523 | 1/1991 | Gardner | 426/268 |

FOREIGN PATENT DOCUMENTS

| | | | |
|---|---|---|---|
| 54-140747 | 11/1979 | Japan | 426/542 |
| 55-118344 | 9/1980 | Japan | 426/270 |
| 2-55785 | 2/1990 | Japan | 426/542 |

*Primary Examiner*—Carolyn Paden
*Attorney, Agent, or Firm*—Cook, Egan, McFarron & Manzo, Ltd.

[57] ABSTRACT

The present invention provides for a composition of natural antioudants comprising tocopherol, ascorbic acid, citric acid and phospholepeds which are useful in oxidation of oils.

25 Claims, No Drawings

COMPOSITION OF NATURAL ANTIOXIDANTS FOR THE STABILIZATION OF POLYUNSATURATED OILS

BACKGROUND OF INVENTION

The present invention relates generally to the prevention of deterioration of food, cosmetic and pharmaceutical products which contain polyunsaturated fatty acids. More particularly, the present invention relates to a natural composition of antioxidants for stabilization of polyunsaturated oils comprising tocopherols, ascorbic acid, citric acid, and phospholipids. The phospholipids may be from soybean or egg. The former is usually called "soybean lecithin" commercially. Rosemary extract can also be added to the composition.

Today, cosmetic and pharmaceutical products containing polyunsaturated fatty acids are manufactured at plants throughout the country, prepackaged for sale, and distributed to supermarkets and convenience stores across the country. Because of the nature of such products and the transportation of such products around the country, these products require a long shelf-life. In order to increase the shelf-life, it is necessary to prevent the deterioration of the quality of the product. One cause of deterioration is oxidation. Oxidation particularly occurs with fat-containing products. For example, oils and fats containing polyunsaturated fatty acids, such as fish oils which contain eicosapentaenoic acid and decosahexaenoic acid, as well as vegetable oils which contain linoleic and/or linolenic acid, are susceptible to oxidation by oxygen in the air to form peroxides. Peroxides decompose to produce volatile compounds with objectionable odors and flavors. For example, fish oil, such as menhaden oil, can quickly develop a green, grassy and fishy odor and flavor. Soybean oil is another product which can also easily oxidize to produce the classical reversion odor and flavor. In addition, such oxidation products may be harmful to human health Even when fish oil, such as menhaden oil, is highly purified to an odorless and flavorless oil, such as that according to the teachings of Chang et al. (U.S. Pat. No. 4,874,629), the oil can still redevelop the green and fishy odor and flavor when it is exposed to even a trace amount of air or oxygen. It has been reported that fish oil, even when packaged in gelatin capsules, can develop relatively high peroxide values during storage.

Accordingly, to use such oils in food, or as a dietary supplement, they must be stabilized to prevent or to retard the development of objectionable odors and flavors, as well as to protect the health of consumers.

Many different antioxidants and antioxidant compositions have been developed over the years. Many of these antioxidants, such as BHA and BHT, are synthetic. Today, people are more health oriented and prefer natural products which are considered safe for human consumption. In addition, synthetic compounds have recently come under heavy scrutiny by the FDA. The natural antioxidant compositions, which have been developed, also suffer from problems which limit their usefulness. For example, EP 0 326 829 (Löllger et al.) discloses a natural mixture of tocopherol, ascorbic acid, and lecithin to protect lipids against oxidation. The mixture, however, may produce a red color in the oil due to the combination of ascorbic acid and lecithin.

Accordingly, it is object of the present invention to provide a composition of natural antioxidants that will retard the oxidation of fats and oils and thus the deterioration of food products. Further, it will have improved antioxidant activity over prior compounds so as to provide better prevention of oxidation and the resulting food deterioration. In addition, the present invention will significantly decrease the undesirable color that results from the combination of ascorbic acid and lecithin in the oils or their products.

SUMMARY OF THE INVENTION

The present invention provides a composition of natural antioxidants comprising tocopherols, ascorbic acid, citric acid and phospholipids. The composition of the antioxidants of the present invention comprises from about 10% to about 62.5% by weight of tocopherols, from about 1.5% to about 20% by weight of ascorbic acid, from about 1.5% to about 20% by weight of citric acid, and from about 26% to about 85% by weight of phospholipids.

The composition preferably comprises about 29.4% tocopherols, about 5.9% ascorbic acid, about 5.9% citric acid, and about 58.8% phospholipids, all by weight.

The composition can further comprise the addition of rosemary extract as described in U.S. Pat. No. 3,950,266 to the other antioxidants listed above. With rosemary extract, the composition of the present invention comprises from about 6.5% to about 54% by weight of tocopherols, from about 1.2% to about 16% by weight of ascorbic acid, from about 1.2% to about 16% by weight of citric acid, from about 17% to about 77% by weight of phospholipids, and from about 6.5% to about 54% by weight of rosemary extract. Preferably, the composition comprises about 22.7% tocopherols, about 4.5% ascorbic acid, about 4.5% citric acid, about 45.5% phospholipids, and about 22.7% rosemary extract, all by weight.

The present invention also provides a composition of natural antioxidants for oils rich in tocopherols comprising ascorbic acid, citric acid, and phospholipids. The composition comprises from about 2% to about 27% by weight ascorbic acid, from about 2% to about 27% by weight citric acid, and from about 56% to about 95% by weight phospholipids. Preferably, the composition comprises about 8.3% ascorbic acid, 8.3% citric acid and 83.4% phospholipids, all by weight. The composition can further comprise the addition of rosemary extract to the other items listed above. With rosemary extract, the composition comprises from about 1.8% to about 23% by weight of ascorbic acid, from about 1.8% to about 23% by weight of citric acid, from about 35% to about 90% by weight of phospholipids, and from about 5% to about 45% by weight of rosemary extract. Preferably, the composition comprises about 6.9% of ascorbic acid, about 6.9% of citric acid, about 70% of phospholipids and about 17.2% of rosemary extract, all by weight.

The composition of the antioxidants of the present invention in a fish oil comprises the following percentages with relation to the oil, from about 0.05% to about 0.2% by weight of tocopherols, from about 0.01% to about 0.04% by weight of ascorbic acid, from about 0.01% to about 0.04% by weight of citric acid, and from about 0.1% to about 0.4% by weight of de-oiled soybean phospholipids. The composition can further comprise rosemary extract in an amount of from about 0.05% to about 0.2% by weight. Preferably, the composition in the fish oil comprises about 0.1% tocopherols, about 0.02% ascorbic acid, about 0.02% citric acid, about 0.2% de-oiled soybean phospholipids and about 0.1% rosemary extract, all by weight.

The composition of the antioxidants of the present invention in a tocopherols rich vegetable oil comprises the following percentages with relation to the oil from about 0.01% to about 0.04% by weight of ascorbic acid, from about 0.01% to about 0.04% by weight of citric acid, and from about 0.1% to about 0.4% by weight of de-oiled soybean phospholipids. The composition can further comprise from about 0.025% to about 0.1% by weight of rosemary extract. Preferably, the composition in the vegetable oils comprises about 0.02% ascorbic acid, about 0.02% citric acid, about 0.2% de-oiled soybean phospholipids, and about 0.05% rosemary extract, all by weight.

The compositions of the present invention may be added to products containing polyunsaturated fatty acids or oils at many different concentrations, depending upon the use to which the products are to be put and the economics of the product. It has been found that the use of from about 0.10 percent to about 0.6 percent by weight, based upon the weight of the unsaturated oils produces useful results, but other concentrations may be used. In a vegetable oil that is not rich in tocopherols, a composition of tocopherol, ascorbic acid, citric acid, phospholipids and possibly rosemary extract could be used.

DESCRIPTION OF THE PREFERRED EMBODIMENT

The present invention is concerned with a combination of natural antioxidants that together through a synergistic effect retard oxidation and the development of a green and fishy odor and flavor that results from the oxidation of polyunsaturated oils such as deodorized fish oils. A composition comprising tocopherols, which is usually a mixture of several tocopherol isomers, ascorbic acid, citric acid, and phospholipids has been found to possess an unexpectantly effective antioxidant property. The phospholipids can be from soybean or egg. Soybean phospholipids are available commercially in various forms and purities and can be used accordingly. A preferred phospholipid is de-oiled soybean phospholipid. The addition of rosemary extract to the composition further enhances the composition's antioxidant property.

No single natural antioxidant, even when used at an amount equal to the total amount of the composition of the present invention, will have the same effect of antioxidant activity as that of the present composition. Further, a composition lacking any of the components of the present invention will also not have the same antioxidant activity that is achieved with the present composition.

A preferred embodiment of the composition of the present invention, especially effective for deodorized and purified fish oil such as menhaden oil, is as follows by weight:

| Tocopherols | 29.4% |
| --- | --- |
| Ascorbic acid | 5.9% |
| Citric acid | 5.9% |
| De-oiled soybean phospholipids | 58.8% |

The preferred amount of the above embodiment for the addition to the menhaden oil is 0.34%. The addition of 0.1% of rosemary extract by weight of the oil can further improve the effectiveness of the antioxidant activity.

Since vegetable oils are usually rich in tocopherols naturally, an example of the composition, especially effective for soybean oil is as follows by weight:

| Ascorbic Acid | 8.3% |
| --- | --- |
| Citric Acid | 8.3% |
| De-oiled soybean phospholipids | 83.4% |

The preferred amount of the above composition for the addition to soybean oil is 0.24% The addition of 0.05% of rosemary extract by weight of the oil can further improve the effectiveness of the antioxidant activity.

The compositions of the present invention can also be used with all omega-3 fatty acids containing oils such as menhaden oil, sardine oil, herring oil, anchovy oil, Pilchard oil, and other such oils. Other possible oils in which the present composition can retard oxidation include vegetable oils, which contain a significant amount of polyunsaturated fatty acid, such as sunflower seed oil, rapeseed oil, canola oil, corn oil, cottonseed oil, and other similar oils. Most vegetable oils already contain a sufficient amount of tocopherols naturally. Therefore, it is not necessary to add any additional tocopherols but rather to only add the other three components (and possibly rosemary extract) to achieve the synergistic effect of the present invention. Furthermore, animal fats such as lard, beef tallow, and butter can benefit by use of the composition of the present invention. Finally, other foods, cosmetic, and pharmaceutical products which contain polyunsaturated fatty acids can also have their oxidation and deterioration retarded by use of the compositions of the present invention.

EXAMPLES OF THE PRESENT INVENTION

The following examples will demonstrate that the compositions of the present invention are clearly superior in the prevention of the deterioration of products containing menhaden oil or vegetable oil than prior compositions or synthetic antioxidants.

In all of the examples, the effectiveness of the antioxidant composition is based on a determination of AOM hours (official method of American Oil Chemists' Society, Cd 12-57) using a recently developed instrument, the Rancimat (Model 617). The Rancimat was used to determine the induction period in hours at various temperatures, and at an air flow rate of 20 liters per hour.

The materials used were as follows:

Menhaden Oil: A refined and double bleached menhaden oil, supplied under the trade name of SPMO by Zapata Haynie Corporation was further deodorized at 100° C. and purified by passing through a silica gel column according to the teaching of Chang, et al. in U.S. Pat. No. 4,879,629.

Soybean Oil: A refined, bleached and deodorized soybean oil supplied by Central Soya Company Inc.

Tocopherols: Natural mixed tocopherols under the trade name of Covi-Ox T70 supplied by the Henkel Corporation.

De-oiled Soybean Phospholipids: Granular soybean lecithin containing 96% of phospholipids, under the trade name of Centrolex R, supplied by Central Soya Company, Inc.

Rosemary Extract: Standard oleoresin extract supplied by Kalsec Inc., under trade name of Herbalox ® O.

EXAMPLE 1

100 g of menhaden oil was used as the control (Sample A in Table 1). Sample B was produced through the addition of 0.1 g of tocopherols dissolved in hexane, 0.02g of ascorbic acid dissolved in anhydrous ethanol, 0.02g of citric acid dissolved in anhydrous ethanol and 0.2g of soybean phospholipids dissolved in hexane, to 100 g of menhaden oil. After mixing well, the solvents were removed with the use of a rotoevaporator under a vacuum and at a temperature below 80° C. Sample C was made through the addition of 0.1 g of rosemary extract, dissolved in a mixture of anhydrous ethanol and hexane (9:1 v/v), to the same formula as was previously prepared in sample B. The rosemary extract was added before the solvents were removed through the use of the rotoevaporator. The induction period for each sample was measured by the use of the rancimat. In addition, the induction period for the menhaden oil with the addition of synthetic antioxidants, BHA and BHT and for the control was also measured.

TABLE 1a

| Sample | Antioxidant Composition Added (% by weight of oil) | | Induction Period (Hours at 90° C.) |
|---|---|---|---|
| A | None | | 0.9 |
| B | Tocopherols | 0.10% | 25.2 |
|   | Ascorbic Acid | 0.02% | |
|   | Citric Acid | 0.02% | |
|   | Soybean Phospholipids | 0.20% | |
| C | Tocopherols | 0.10% | 26.4 |
|   | Ascorbic Acid | 0.02% | |
|   | Citric Acid | 0.02% | |
|   | Soybean Phospholipids | 0.20% | |
|   | Rosemary Extract | 0.10% | |
| D | BHA | 0.02% | 2.1 |
| E | BHT | 0.02% | 1.7 |

Table 1a clearly shows that the induction period for the compositions of the present invention is much higher than that for Sample A which had no antioxidant added. Further, the synthetic antioxidants, at the maximum amount allowed by the FDA, have a very low induction period, not much higher than the induction period of Sample A, and considerably lower than the induction period for Samples B and C. In order to further demonstrate the antioxidant activity of the compositions, samples A, B, C, and D of Example 1 were aged at 45° for one week and for two weeks. The peroxide values of the samples, after aging is shown in Table 1b.

TABLE 1b

| Sample | Antioxidant Added (% by weight of oil) | | Peroxide Value (meq./k.) (after aging at 45° C. for 7 or 14 days) | |
|---|---|---|---|---|
|   |   |   | 7 days | 14 days |
| A | None | | 16.8 | 24.0 |
| B | Tocopherols | 0.10% | 0.9 | 7.9 |
|   | Ascorbic Acid | 0.02% | | |
|   | Citric Acid | 0.02% | | |
|   | Soybean Phospholipids | 0.20% | | |
| C | Tocopherols | 0.10% | 1.5 | 6.0 |
|   | Ascorbic Acid | 0.02% | | |
|   | Citric Acid | 0.02% | | |
|   | Soybean Phospholipids | 0.20% | | |
|   | Rosemary Extract | 0.10% | | |
| D | BHA | 0.02% | 14.3 | 23.0 |

As in the samples in Table 1a, no antioxidant has been added to Sample A, the antioxidant compositions of the present invention have been added to Samples B and C, and the synthetic antioxidant, BHA has been added to Sample D. Peroxides being the compounds which decompose to produce volatile compounds with objectionable odors and flavors, it is desirable to have a low peroxide value. Note, that Samples B and C of the present invention have a much lower peroxide value than that of the Samples A or D. Accordingly, the results of this example clearly show that the compositions of the present invention significantly retard the oxidation and the resulting deterioration of oil and do so much more effectively than a synthetic antioxidant.

EXAMPLE 2

Five samples of menhaden oil with antioxidants added were prepared in the same manner as in Example 1. The composition of Sample C of Example 1 was used as the "standard" for this Example. Samples 1 through 5 were produced from the same composition as the "Standard", except that one of the five components of the composition (Sample C of Example 1) was eliminated. The induction period for each sample was then measured and compared to a composition having all five components (Standard).

TABLE 2

| Sample | Antioxidant Added | Induction Period (Hours at 90° C.) |
|---|---|---|
| Control | None | 0.9 |
| Standard | Sample C of Example 1 | 26.4 |
| 1 | Elimination of Rosemary Extract | 25.2 |
| 2 | Elimination of Tocopherols | 11.8 |
| 3 | Elimination of Ascorbic Acid | 10.5 |
| 4 | Elimination of Citric Acid | 24.1 |
| 5 | Elimination of Soybean Phospholipids | 15.6 |

Table 2 clearly demonstrates that the compositions of the present invention, as represented in the Standard Sample and Sample 1, have a much higher induction period than any of the compositions having one of the components eliminated. Citric acid, as shown in Table 2, does not have a strong effect on antioxidant activity. However, it is important in the prevention of the development of an off-color.

EXAMPLE 3

The composition of Sample C of Example 1, with all five components, was used as the standard. Five samples of menhaden oil were also prepared in the same manner as in Example 1. In each sample, one of the components of the composition of the present invention (Standard) was added at a concentration of 0.44%. The induction period of each of the samples was measured.

TABLE 3

| Sample | Antioxidant Added (% by weight of oil) | Induction Period (Hours at 90° C.) |
|---|---|---|
| Control | None | 0.9 |
| Standard | Sample C of Example 1 | 26.4 |
| 1 | Tocopherols, 0.44% | 2.3 |
| 2 | Ascorbic Acid, 0.44% | 1.4 |
| 3 | Citric Acid, 0.44% | 1.0 |
| 4 | De-oiled soybean phospholipids 0.44% | 1.3 |
| 5 | Rosemary extract, 0.44% | 6.9 |

Table 3 shows that each of the five components of the composition of the present invention, when added singularly, even at a concentration higher than the total amount of the five components in the Standard, does not produce an effective antioxidant activity. Thus indicating clearly that the composition of the present invention has an unusual strong antioxidant activity due to synergism.

EXAMPLE 4

The composition of the present invention has another novel advantage. The amount of phospholipids used in the present invention should be sufficient to cause the amount of ascorbic acid used in the present invention to be soluble in the oil. This makes the ascorbic acid, which is otherwise insoluble in oil, more evenly distributed into the oil and hence makes the antioxidant activity of the ascorbic acid more effective.

The unexpected but distinctive effect of phospholipids on the solubility of ascorbic acid in oils can be clearly demonstrated by the following simple example. Ten grams of ascorbic acid were dissolved in one liter of anhydrous ethanol at 60° C. and 100 grams of de-oiled soybean phospholipids [Centrolex R] were dissolved in 250 ml of hexane. The two solutions were thoroughly mixed and the solvents were then removed with the use of a rotoevaporator, under vacuum, at a temperature below 60° C. A hexane-soluble, brownish-yellow powder was obtained. It should be noticed that the ascorbic acid was originally insoluble in hexane, but after it was combined with the soybean phospholipids, the brownish-yellow powder obtained was completely soluble in hexane. This hexane solution can then be easily added into an oil such as a fish oil or vegetable oil. After the solvent is removed, a clear oil solution of ascorbic acid is obtained.

A commercial product, ascorbyl palmitate, manufactured by Hoffmann La Roche Inc. has a better oil solubility than ascorbic acid. However, the ascorbyl palmitate still cannot directly dissolve in oil. It has to be dissolved in a solvent, such as ethanol, and then dissolve the solution in oil. The ethanol will have to be removed in order to obtain a clear solution of the ascorbyl palmitate in the oil. Further, the loss of one hydroxyl group from the ascorbic acid molecule by the reaction with the palmitic acid makes the ascorbyl palmitate less effective as an antioxidant.

In order to demonstrate the above mentioned novel advantage of the present invention, another set of samples was prepared in the same manner as that described in Example 1. Samples A, B, C and D were exactly the same as described in Example 1. However, an additional sample B-PA was added. This sample (BPA) was the same as Sample B except that the ascorbic acid was replaced by ascorbyl palmitate. Since ascorbyl palmitate has a larger molecular weight than ascorbic acid and in order for it to be equivalent to 0.02% of ascorbic acid in moles, 0.04% of ascorbyl palmitate was used.

The results of the induction period of the above mentioned samples, as shown in Table 4, clearly indicates that ascorbic acid is more effective than ascorbyl palmitate in the invented antioxidant composition.

TABLE 4

| Sample | Antioxidant Added (% by weight of oil) | | Induction Period (Hours at 90° C.) |
| --- | --- | --- | --- |
| A | None | | 0.9 |
| B | Ascorbic Acid | 0.02% | 25.2 |
| | Tocopherols | 0.10% | |
| | Citric Acid | 0.02% | |
| | Soybean Phospholipids | 0.20% | |
| B-AP | Ascorbyl Palmitate | 0.04% | 18.8 |

TABLE 4-continued

| Sample | Antioxidant Added (% by weight of oil) | | Induction Period (Hours at 90° C.) |
| --- | --- | --- | --- |
| | Tocopherols | 0.10% | |
| | Citric Acid | 0.02% | |
| | Soybean Phospholipids | 0.20% | |
| C | BHA | 0.02% | 2.1 |
| D | BHT | 0.02% | 1.7 |

EXAMPLE 5

The present invention is equally effective when applied to vegetable oils, such as refined, bleached, and deodorized soybean oil. Since vegetable oils are generally rich in tocopherols, no additional tocopherols were added. The samples were prepared in the same manner as those in Example 1 except that menhaden oil was replaced by refined, bleached and deodorized soybean oil.

TABLE 5

| Sample | Antioxidant Added (by weight of oil) | | Induction Period (hours at 110° C.) |
| --- | --- | --- | --- |
| A | None | | 6.50 |
| B | Ascorbic Acid | 0.02% | 13.15 |
| | Citric Acid | 0.02% | |
| | Soybean Phospholipids | 0.20% | |
| C | BHA | 0.02% | 6.50 |
| D | BHT | 0.02% | 6.60 |

Table 5 shows the induction period of these samples. The sample of the composition of the present invention (Sample B) has a much greater induction period than the synthetic antioxidants (Sample C and D) or the sample with no antioxidant (Sample A).

EXAMPLE 6

The unusual antioxidant activity of the composition of the present invention, when used in soybean oil, is demonstrated, in a manner similar to that used for menhaden oil (in Example 2), by the following results.

TABLE 6

| | Antioxidant Added (%)* | | | | Induction Period (Hours at 100° C.) |
| --- | --- | --- | --- | --- | --- |
| Sample | Rosemary Extract | Ascorbic Acid | Citric Acid | De-oiled Soybean Phospholipids | |
| Control | 0.00 | 0.00 | 0.00 | 0.00 | 14.6 |
| Standard** | 0.05 | 0.02 | 0.02 | 0.20 | 28.8 |
| 1 | 0.00 | 0.02 | 0.02 | 0.20 | 25.0 |
| 2 | 0.05 | 0.00 | 0.02 | 0.20 | 21.3 |
| 3 | 0.05 | 0.02 | 0.00 | 0.20 | 27.4 |
| 4 | 0.05 | 0.02 | 0.02 | 0.00 | 24.6 |

*By weight of the oil.
**A composition of the present invention.

EXAMPLE 7

This example was intended to show the superiority of the composition of the present invention over the three component composition of the prior art. The three component composition of the Löllger patent contained 0.1% tocopherol, 0.02% ascorbic acid, and 0.2% lecithin. The antioxidants from each composition were added to refined and bleached menhaden oil. In the four component composition of the present invention, 0.02% by weight citric acid was added to the components of the three component system of Löllger.

TABLE 7

| ANTIOXIDANTS ADDED* to Menhaden Oil (refined and bleached) | | Lovibond Color (5¼" cell) | |
|---|---|---|---|
| | | Red | Yellow |
| None | | 0.6 | 10.4 |
| Ternary System as Löllger's Patent | Tocopherol 0.10% Ascorbic Acid 0.02% Lecithin 0.20% | 3.7 | 27.7 |
| Four Component composition of the present invention | Tocopherol 0.10% Ascorbic Acid 0.02% Lecithin 0.20% Citric Acid 0.02% | 1.1 | 17.7 |

*(% by weight of oil)

Table 7 shows the difference in color between the three component composition of Löllger's patent and the four component composition of the present invention. Löllger's composition gives a much greater red color, which is undesirable, than the color resulting from the utilization of the present invention. The avoidance of the red color is considered of great importance to the quality of the oil. A difference in one unit of Lovibond color is significant. Accordingly, the compositions of the present invention, through the addition of citric acid (and rosemary extract in the five component composition), have at least three advantages over the prior art:

(1) Significantly decreases the undesirable color developed by the combination of ascorbic acid and lecithin;

(2) Has improved antioxidant activity as shown in Table 2 of Example 2, the elimination of citric acid decreases the induction period of the four component system from 26.4 to 24.1 hours; and (3) Uses a much lower amount of "Lecithin". In all the examples of Löllger's patent, 1% of "Lecithin" was used. Such a high amount of "Lecithin" will impart an undesirable odor and flavor to the product.

The scope of the invention herein shown and described is to be considered only as illustrative. It will be apparent to those skilled in the art that numerous modifications may be made therein without departure from the spirit of the invention or the scope of the appended claims.

We claim:

1. A natural antioxidant composition for stabilization of polyunsaturated oils comprising an amount of tocopherol, an amount of ascorbic acid, an amount of citric acid and an amount of phospholipid which is effective to stabilize polyunsaturated oils.

2. An antioxidant composition as described in claim 1 having tocopherols in an amount of from about 10% to about 62.5% by weight, ascorbic acid in an amount of from about 1.5 to about 20% by weight, citric acid in an amount of from about 1.5% to about 20% by weight, and phospholipids in an amount of from about 26% to about 85% by weight.

3. An antioxidant composition as described in claim 2, wherein the amount of tocopherols is about 29.4% by weight, the amount of ascorbic acid is about 5.9% by weight, the amount of citric acid is about 5.9% by weight, and the amount of phospholipids is about 58.8% by weight.

4. An antioxidant composition as described in claim 1 further comprising rosemary extract in an amount effective to further stabilize polyunsaturated oils.

5. An antioxidant composition as described in claim 4 having tocopherols in an amount of from about 6.5% to about 54% by weight, ascorbic acid in an amount of from about 1.2% to about 16% by weight, citric acid in an amount of from about 1.2% to about 16% by weight, phospholipids in an amount of from about 17% to about 77% by weight, and rosemary extract in an amount of from about 6.5% to about 54% by weight.

6. An antioxidant composition as described in claim 5 wherein the amount of tocopherols is about 22.7% by weight, the amount of ascorbic acid is about 4.5% by weight, the amount of citric acid is about 4.5% by weight, the amount of phospholipids is about 45.5% by weight, and the amount of rosemary extract is about 22.7% by weight.

7. A natural antioxidant composition for stabilization of polyunsaturated oils comprising an amount of tocopherol, an amount of ascorbic acid, an amount of citric acid, an amount of soybean phospholipids, and an amount of rosemary extract which is effective to stabilize polyunsaturated oils.

8. An antioxidant composition as described in claim 7 having tocopherols in an amount of from about 6.5% to about 54% by weight, ascorbic acid in an amount of from about 1.2% to about 16% by weight, citric acid in an amount of from about 1.2% to about 16% by weight, soybean phospholipids in an amount of from about 17% to about 77% by weight, and rosemary extract in an amount of from about 6.5% to about 54% by weight.

9. An antioxidant composition as described in claim 8, wherein the amount of tocopherols is about 22.7% by weight, the amount of ascorbic acid is about 4.5% by weight, the amount of citric acid is about 4.5% by weight, the amount of soybean phospholipids is about 45.5% by weight, and the amount of rosemary extract is about 22.7% by weight.

10. A natural antioxidant composition for stabilization of an oil rich in tocopherols comprising an amount of ascorbic acid, an amount of citric acid and an amount of phospholipids which is effective to stabilize an oil rich in tocopherols.

11. An antioxidant composition as described in claim 10 having ascorbic acid in an amount of from about 2% to about 27% by weight, citric acid in an amount of from about 2% to about 27% by weight, and phospholipids in an amount of from about 56% to about 95% by weight.

12. An antioxidant composition as described in claim 11 wherein the amount of ascorbic acid is about 8.3% by weight, the amount of citric acid is about 8.3% by weight and the amount of phospholipids is about 83.4% by weight.

13. An antioxidant composition as described in claim 10 further comprising rosemary extract in an amount effective to further stabilize an oil rich in tocopherols.

14. An antioxidant composition as described in claim 13 having ascorbic acid in an amount of from about 1.8% to about 23% by weight, citric acid in an amount from about 1.8% to 23% by weight, phospholipids in an amount of from about 35% to about 90% by weight, and rosemary extract in an amount of from about 5% to about 45% by weight.

15. An antioxidant composition as described in claim 12 wherein the amount of ascorbic acid is about 6.9% by weight, the amount of citric acid is about 6.9% by weight, the amount of phospholipids is about 70% by weight, and the amount of rosemary extract is about 17.2% by weight.

16. A natural antioxidant composition for stabilization of an oil rich in tocopherols comprising an amount of ascorbic acid, an amount of citric acid, an amount of soybean phospholipids, and an amount of rosemary extract which ic effective to stabilize an oil rich in tocopherols.

17. An antioxidant composition as described in claim 16 having ascorbic acid in an amount of from about 1.8% to about 23% by weight, citric acid in an amount of from about 1.8% to about 23% by weight, soybean phospholipids in an amount of from about 35% to about 70% by weight, and rosemary extract in an amount of from about 5% to about 45% by weight.

18. An antioxidant composition as described in claim 17 wherein the amount of ascorbic acid is about 6.9% by weight, the amount of citric acid is about 6.9% by weight, the amount of soybean phospholipids is about 83.4% by weight and the amount of rosemary extract is about 17.2% b weight.

19. A fish oil containing an antioxidant composition which comprises tocopherols in an amount of from about 0.05% to about 0.2% by weight, ascorbic acid in an amount of from about 0.01% to about 0.04% by weight, citric acid in an amount of from about 0.01% to about 0.04% by weight and de-oiled soybean phospholipids in an amount of from about 0.1% to about 0.4%, all by weight of the fish oil.

20. A fish oil containing an antioxidant composition as described in claim 19 further comprising rosemary extract in an amount of from about 0.05% to about 0.2% by weight of the fish oil.

21. A fish oil containing an antioxidant composition as described in claim 20 having tocopherols in an amount of about 0.1% by weight, ascorbic acid in an amount of about 0.02% by weight, citric acid in an amount of about 0.02% by weight, de-oiled soybean phospholipids in an amount of about 0.2% by weight, and rosemary extract in an amount of about 0.1%, all by weight of the fish oil.

22. A tocopherols rich vegetable oil containing an antioxidant composition comprising ascorbic acid in an amount of from about 0.01% to about 0.04% by weight, citric acid in an amount of from about 0.01% to about 0.04% by weight, and de-oiled soybean phospholipids in an amount of from about 0.1% to about 0.4%, all by weight of the vegetable oil.

23. A vegetable oil containing an antioxidant composition as described in claim 22 further comprising rosemary extract in an amount of from about 0.25% to about 0.1% by weight of the vegetable oil.

24. A vegetable oil containing an antioxidant composition as described in claim 23 having ascorbic acid in an amount of about 0.02% by weight, citric acid in an amount of about 0.02% by weight, de-oiled soybean phospholipids in an amount of about 0.2% by weight, and rosemary extract in an amount of about 0.05%, all by weight of the vegetable oil.

25. A vegetable oil antioxidant composition comprising an amount of tocopherol, an amount of ascorbic acid, an amount of citric acid and an amount of phospholipids which is effective to stabilize a vegetable oil.

* * * * *